(12) United States Patent
Anderson et al.

(10) Patent No.: US 6,743,943 B2
(45) Date of Patent: Jun. 1, 2004

(54) POLYMERIZABLE HALOGENATED VINYL ETHERS

(75) Inventors: Russell F. Anderson, Cook County, IL (US); David E. Bradley, Erie County, NY (US); David Nalewajek, Erie County, NY (US); Haridasan K. Nair, Erie County, NY (US); Mariola J. Proszowski, Cook County, IL (US); Eugene V. Sitzman, Cook County, IL (US); Ellen L. Swan, Erie County, NY (US)

(73) Assignee: Honeywell International Inc., Morristown, NJ (US)

( * ) Notice: Subject to any disclaimer, the term of this patent is extended or adjusted under 35 U.S.C. 154(b) by 66 days.

(21) Appl. No.: 09/854,244

(22) Filed: May 11, 2001

(65) Prior Publication Data

US 2001/0034458 A1 Oct. 25, 2001

Related U.S. Application Data

(60) Division of application No. 09/271,650, filed on Mar. 18, 1999, which is a continuation-in-part of application No. 09/218,201, filed on Dec. 22, 1998, and a continuation-in-part of application No. 09/009,110, filed on Jan. 20, 1998, now Pat. No. 6,133,472.
(60) Provisional application No. 60/113,207, filed on Dec. 22, 1998.

(51) Int. Cl.$^7$ .............................................. C07C 69/34
(52) U.S. Cl. ....................... 560/198; 560/181; 560/182; 560/183; 560/184
(58) Field of Search ................................ 560/198, 181, 560/182, 183, 184

(56) References Cited

PUBLICATIONS

Revesz, M, et al Acta Chimica Hungarica (1992) 129 (2) 287–95.*

\* cited by examiner

Primary Examiner—Paul J. Killos
(74) Attorney, Agent, or Firm—Deborah Chess

(57) ABSTRACT

Vinyl ether compounds having the formula:

$$R-O-X-O-CH=CH_2$$

wherein R is a radical selected from $R_1-C_nH_m-$, $R_1-C_nH_m-C(=O)-$, $R_1-C_nH_m-CH[-O-X-O-CH=CH_2-]$, $R_1-C_nH_m-CH[-O-X-O-CH=CH_2-]C(=O)-$, $R_1-C_nH_m-CH[-C(=O)-O-X-O-CH=CH_2-]$, $R_1-C_nH_m-CH[-C(=O)-O-X-O-CH=CH_2-]C(=O)-$, $R_1-[CFCl-CF_2-]_pCH_2-$ and $HCFCl-CF_2-$, wherein $R_1$ is hydrogen, an unsubstituted or substituted fluorinated aliphatic radical, an unsubstituted or substituted fluorinated cyclic aliphatic radical, an unsubstituted or substituted fluorinated aromatic radical, an unsubstituted or substituted fluorinated araliphatic radical, or an unsubstituted or substituted fluorinated heterocyclic radical; n is an integer between 1 and 6, inclusive; $n \leq m \leq 2n$; p is an integer between 1 and 20, inclusive and X is an unsubstituted or substituted aliphatic radical, an unsubstituted or substituted cyclic aliphatic radical, an unsubstituted or substituted aromatic radical, an unsubstituted or substituted araliphatic radical, or an unsubstituted or substituted heterocyclic radical; provided that when $R_1$ of $R_1-C_nH_m-$ is an otherwise unsubstituted fluorinated aliphatic group, X is not ethylene or propylene. Curable compositions containing the vinyl ether compounds are also disclosed, as well as polymers polymerized from the vinyl ether compounds.

12 Claims, No Drawings

POLYMERIZABLE HALOGENATED VINYL ETHERS

CROSS REFERENCE TO RELATED APPLICATIONS

This application is a divisional of application Ser. No. 09/271,650 filed Mar. 18, 1999

This application is a Continuation-In-Part of U.S. patent application Ser. No. 09/218,201, filed Dec. 22, 1998. This application is also a Continuation-In-Part of U.S. patent application Ser. No. 09/009,110, filed on Jan. 20, 1998 now U.S. Pat. No. 6,133,472. Furthermore, this application claims priority benefit of U.S. Provisional Patent Application Serial No. 60/113,207, filed on Dec. 22, 1998. The disclosures of all three applications are incorporated herein by reference.

FIELD OF INVENTION

The present invention relates to useful halogenated compounds. More specifically, this invention relates to a family of halogenated vinyl ether compounds, their uses, and the products resulting from their use.

BACKGROUND OF THE INVENTION

Vinyl ethers containing fluorine and also chlorine are of particular interest in coatings applications because they form polymers and copolymers that exhibit beneficial properties, including high chemical and thermal resistance, high electrical resistivity, low surface energy and low refractive index. These properties can be imparted to a coating surface and, consequently, halogenated vinyl ethers are particularly useful in making protective coatings, release coatings, as well as, surfactants, anticorrosion agents, antioxidizing agents and the like.

Some fluorinated chemical compounds are known in the art which contain oxyvinyl groups such as are described in U.S. Pat. No. 2,732,370 under the generic formula $C_nF_{2n+1}CH_2$—O—CH=$CH_2$. The fluorinated structures near the oxyvinyl group are believed either not to be radiation curable or not to have radiation curable reactivities to the extent desired.

JP 2,000,721 discloses aliphatic fluorinated vinyl ether compounds having the structure R'R"CH—O—$CH_2CH_2$—O—CH=$CH_2$ wherein R' is a hydrogen, a lower alkyl group or a polyfluoroalkyl group and R" is a polyfluoroalkyl group. U.S. Pat. No. 5,012,011 discloses the synthesis of fluorinated vinyl ethers such as $CF_3(CF_2)_xR_1OCH_2CH(OH)R_2OCH=CH_2$ ($R_1$=C1–C20 alkylene, alkoxyethylene, arylene, aryloxyalkylene; $R_2$=C1–C100 divalent organic radicals; and x=1–22). Fluorinated vinyl compounds containing a hydroxyl or alkoxy group are described by U.S. Pat. No. 4,559,179. The preparation of H($CF_2CF_2$)$_n$$CH_2OCH$=$CH_2$ (n=2–4) is reported by Sukhinin et al., Zh. Vses. khim. O-va., 26(3), 344–5 (1981). Because of the heavily fluorinated structure, adherence to substrates and compatibility with solvents and cosolutes may not be as good as desired.

Moreover, vinyl ether monomers or copolymers that can be cured via ultraviolet (UV) radiation offer even more advantages in coatings and other applications. Photocuring technology has grown rapidly within the last decade. The photocuring process involves the radiation induced polymerization or cross linking of monomers into a three dimensional network and has a number of advantages including the environmentally safe, solvent-free 100% conversion to a desired product, as well as short cycle times and limited space and capital equipment requirements.

In the telecommunications industry, for example, there is a need to develop photocurable compositions for optical wave guide and interconnect applications. In order to be useful in these applications, the photocurable compositions must polymerize to form polymers that are highly transparent at the working wavelength and possess low intrinsic absorption and scattering loss.

U.S. Pat. No. 5,274,174 discloses a new class of photocurable compositions comprised of certain fluorinated monomers, such as diacrylates with perfluoro or perfluoropolyether chains, which possess low intrinsic absorption loss. It is, therefore, possible to make low loss optical interconnects from a photocurable system including these materials.

Fluorine substitution in the polymer structure, however, also induces some other less desirable changes in the polymer's physical properties. One such change is the decrease in refractive index. For a highly fluorinated acrylate photopolymer, the refractive index decreases to the 1.32 region when the H/F mole ratio reaches 0.25. For optical interconnect applications, to avoid loss of light, it is important that the refractive index of the core of a planar waveguide approximate and preferably match that of the optical fiber (generally 1.45).

It is also important to be able to precisely control and fine tune the refractive index of the photopolymer at the working wavelength in optical waveguide and interconnect applications. A desired index of refraction can be produced by mixing photocurable monomers with different refractive indices. Most photopolymers made from conventional photocurable monomers have refractive indices in the region of 1.45–1.55. Depending on the application, it is often desirable to lower a photopolymer's refractive index. One way to do this is to mix low refractive index fluorinated monomers with conventional hydrocarbon-based monomers. Unfortunately, this is difficult to accomplish because of the incompatibility or insolubility of the different monomer systems. Thus, there is a need for photocurable compositions which: (i) possess low intrinsic absorption loss in the near-infrared region; (ii) possess a refractive index approaching traditional optical fibers; and (iii) are compatible with both conventional hydrocarbon-based and highly fluorinated monomers.

DETAILED DESCRIPTION OF THE INVENTION

The present invention provides a family of halogenated vinyl ether compounds which are useful for making other compounds, including polymeric compounds, having a wide variety of uses. The vinyl ether compounds of the present invention exhibit the beneficial properties of fluorinated monomers and can be utilized to realize the benefits of photocuring processes.

These novel compounds are readily radiation curable and curable by other means. These compounds are soluble with other components (cosolutes) and in numerous recoverable and re-useable solvents, and can be formulated to be of low viscosity when applied.

The novel fluorine containing compounds provide enhanced surface properties, and are fast curing but have indefinite pot life before exposure to radiation or other curing processes. The compounds, when cured, have a low refractive index. The compounds have good substrate adhesion, and can be chemically bonded into other resins, eliminating migratory problems associated with materials which are not bonded into a formulation. In addition, the compounds can be made from commercially available materials by both known and novel processes. The compounds of the invention include oxyvinyl monoethers, oxyvinyl diethers, oxyvinyl monoesters and oxyvinyl diesters of fluorine containing structures.

In general the compounds of the invention have the general formula:

$$R\text{—}O\text{—}X\text{—}O\text{—}CH\text{=}CH_2 \qquad (I)$$

wherein R is radical having a formula selected from: $R_1\text{—}C_nH_m\text{—}$, $R_1\text{—}C_nH_m\text{—}C(\text{=}O)\text{—}$, $R_1\text{—}C_nH_mCH[\text{—}O\text{—}X\text{—}O\text{—}CH\text{=}CH_2]\text{—}$, $R_1\text{—}C_nH_mCH[\text{—}O\text{—}X\text{—}O\text{—}CH\text{=}CH_2]\text{—}C(\text{=}O)\text{—}$, $R_1\text{—}C_nH_mCH[\text{—}C(\text{=}O)\text{—}O\text{—}X\text{—}O\text{—}CH\text{=}CH_2]\text{—}$, $R_1\text{—}C_nH_mCH[\text{—}C(\text{=}O)\text{—}O\text{—}X\text{—}O\text{—}CH\text{=}CH_2]\text{—}C(\text{=}O)\text{—}$, $R_1\text{—}[CFCl\text{—}CF_2\text{—}]_pCH_2\text{—}$ and $HCFCl\text{—}CF_2\text{—}$, wherein $R_1$ is hydrogen, an unsubstituted or substituted fluorinated aliphatic radical, an unsubstituted or substituted fluorinated cyclic aliphatic radical, an unsubstituted or substituted fluorinated aromatic radical, an unsubstituted or substituted fluorinated araliphatic radical, or an unsubstituted or substituted fluorinated heterocyclic radical; X is an unsubstituted or substituted aliphatic radical, an unsubstituted or substituted cyclic aliphatic radical, an un-substituted or substituted aromatic radical, an unsubstituted or substituted araliphatic radical, or a unsubstituted or substituted heterocyclic radical; n is between 1 and 6, inclusive; $n \leq m \leq 2n$; and p is from 1 to 20, inclusive; provided that when $R_1$ of $R_1\text{—}C_nH_m\text{—}$ is a fluorinated aliphatic radical, X is not an ethylene or propylene radical.

Fluorinated oxyvinyl diethers of the invention may be represented by the formula:

$$R_1C_nH_m[OXOCH\text{=}CH_2]_2$$

Fluorinated oxyvinyl monoesters of the invention may be represented by the formula:

$$R_1C_nH_mCOOXOCH\text{=}CH_2$$

Fluorinated oxyvinyl diesters of the invention may be represented by the formula:

$$R_1C_nH_mCH[COOXOCH\text{=}CH_2]_2$$

Another aspect of the present invention provides curable compositions that contain a curable component that includes at least one compound having the structure of Formula I, in which R and X are as described above for Formula I. Preferred curable compositions include photocurable compositions combining at least one compound having the structure of Formula I and a photo initiator compound.

The curable compositions will contain between about 0.01% to about 99% by weight of at least one compound having the structure of Formula I. For waveguide coatings for example, the curable composition should contain at least 35% by weight of at least one compound having the structure of Formula I.

It has been unexpectedly discovered that the compounds having the structure of Formula I, when added at levels less than about 10% by weight to other curable systems, are cross-linked into the cured polymer, yet are oriented toward the surface of a polymer coating, providing useful modifications to the surface properties. A level between about 0.1% and about 2.0% by weight is preferred. This aspect of the present invention may also be employed with compounds having the structure of Formula I wherein R is a radical having the formula $R_1\text{—}CFH\text{—}CF_2\text{—}$ or $R_1\text{—}CF\text{=}CF\text{—}$, wherein $R_1$ and X are the same as described above with respect to Formula I.

The photocurable compositions of the present invention are useful in the manufacture of optical devices having light transmissive regions. Therefore, another aspect of the present invention provides a process for producing an optical device employing the steps of: (a) applying a layer of the photocurable composition of the invention onto a substrate; (b) imagewise exposing the photocurable composition of the invention to actinic radiation to form exposed and non-exposed areas on the substrate; and (c) removing the imagewise non-exposed areas while leaving the imagewise exposed areas on the substrate.

The invention further includes uses of the halogenated vinyl ether compounds of the present invention in coatings, inks, adhesives, structural polymers and optical devices, including fiber optics and waveguides, and to make photocured products using photocuring processes. A preferred aspect of this embodiment of the invention comprises the use of the compounds of the present invention in the preparation of the light transmissive component of an optical device, particularly a waveguide.

The present invention also includes polymers produced by curing the fluorinated vinyl ether compounds of the present invention. Therefore, a further aspect of the invention provides a polymer with one or more vinyl ether repeating units having the structure of Formula II:

(II)

wherein R and X are as described above with respect to Formula I.

In Formulae I and II, X is preferably an unsubstituted or substituted $C_1$–$C_{20}$ aliphatic radical, an unsubstituted or substituted $C_3$–$C_{20}$ cyclic aliphatic radical, an unsubstituted or substituted $C_6$–$C_{15}$ aromatic radical, an unsubstituted or substituted $C_7$–$C_{13}$ araliphatic radical, or an unsubstituted or substituted 3–10 member heterocyclic radical. More preferably, X is an unsubstituted or substituted $C_1$–$C_{20}$ alkyl radical, an unsubstituted or substituted $C_3$–$C_{10}$ cycloalkyl radical, an unsubstituted or substituted 3–6 member heterocyclic radical, an unsubstituted or substituted $C_6$–$C_{15}$ aryl radical, or an unsubstituted or substituted $C_7$–$C_{13}$ aralkyl radical. The radicals may be substituted with essentially any conventional organic moiety. Examples of substitution groups include $C_1$–$C_6$ aliphatics such as alkyls, halogenated alkyls, alkoxys, and alkenyls, $C_6$–$C_{15}$ aryls, halogens, particularly fluorine, $C_3$–$C_8$ cyclic aliphatics, nitros, aminos (primary and secondary), amidos, cyanos and hydroxyls.

X as a $C_1$–$C_{20}$ alkyl radical may be straight chain or branched, for example, a methyl, ethyl, n-propyl, isopropyl, n-butyl, isobutyl, tert-butyl, n-pentyl, neopentyl, n-hexyl, n-heptyl, n-octyl, or 2-ethylhexyl radical. Any of these groups may be substituted with typical organic moieties, such as methoxy, ethoxy, n-propoxy, isopropoxy, n-butoxy, methanesulphonyl, cyano, bromine, chlorine or fluorine to form, for example, methoxymethyl, 2-methoxyethyl, 2-ethoxymethyl, 2-n-butoxyethyl, 3-methoxypropyl, 1-methoxybutyl, 2-methoxybutyl, methanesulphonylmethyl, 2-methanesulphonylethyl, 2-cyanoethyl, 2-fluoroethyl, 2,2,2-trifluoroethyl, trichloromethyl, 2-chloroethyl, 2-(chloromethyl)ethyl, 2,2, 2-trichloroethyl, 2-chloro-n-propyl or 3-chloro-n-butyl. In a preferred class of alkyl radicals, X is a straight chain $C_2$–$C_6$ alkyl radical, especially an ethyl or butyl radical.

X as a $C_3$–$C_{10}$ cycloalkyl radical may be, for example, a cyclopropyl, cyclobutyl, cyclopentyl, methylcyclopentyl, cyclohexyl, methylcyclohexyl dimethylcyclohexyl, cycloheptyl, or cyclooctyl radical. Any of these groups may be substituted with essentially any conventional organic radical, including, for example, methoxy, ethoxy, n-propoxy, isopropoxy, n-butoxy, cyano, chlorine or fluorine. In a preferred class of cycloalkyl radical, X is a $C_6$–$C_{10}$ cycloalkyl radical. In a preferred class of cycloalkyl radical, X is a $C_6$–$C_8$ cycloalkyl radical, even more preferably, a cyclohexyldimethyl radical.

X as a 3–6 ring member heterocyclic radical may include known heterocyclic atoms such as N, O and S. Suitable heterocycles include, for example, pyran, thiophene, pyrrole, furan, pyridine, or derivatives thereof.

X as a $C_6$–$C_{15}$ aryl may be, for example, phenyl, o-tolyl, m-tolyl, p-tolyl, o-xylyl, m-xylyl, p-xylyl, alpha-naphthyl or beta naphthyl. Any of these groups may be substituted with essentially any conventional organic radical, for example, halogens, particularly fluorine, $C_1$–$C_4$ alkoxyl or nitro. In a preferred class of compounds, X is $C_6$–$C_{12}$ aryl, especially phenyl or naphthyl.

X as a $C_7$–$C_{20}$ aralkyl radical may be, for example, benzyl, 4-methylbenzyl, o-methylbenzyl, p-methylbenzyl, diphenyl-methyl, 2-phenylethyl, 2-phenylpropyl or 3-phenylpropyl, preferably $C_7$–$C_9$ aralkyl, especially benzyl.

In a still more preferred embodiment, X is an alkyl or aralkyl radical, especially a ethyl, butyl, or cyclohexyldimethyl radical.

For R of Formulae I and II, $R_1$ is preferably hydrogen, an unsubstituted or substituted fluorinated $C_1$–$C_{12}$ aliphatic radical, an unsubstituted or substituted fluorinated $C_3$–$C_{20}$ cyclic aliphatic radical, an unsubstituted or substituted fluorinated $C_6$–$C_{15}$ aromatic radical, an unsubstituted or substituted fluorinated $C_7$–$C_{13}$ araliphatic radical, or an unsubstituted or substituted 3–10 member fluorinated heterocyclic radical. More preferably, $R_1$ is an unsubstituted or substituted fluorinated $C_1$–$C_{12}$ alkyl radical, an unsubstituted or substituted fluorinated $C_3$–$C_{11}$ cycloalkyl radical, an unsubstituted or substituted 3–6 member fluorinated heterocyclic radical, an unsubstituted or substituted fluorinated $C_6$–$C_{15}$ aryl radical, or an unsubstituted or substituted fluorinated $C_7$–$C_{20}$ aralkyl radical. Examples of substitution groups include $C_1$–$C_6$ aliphatics such as alkyls, alkyl ethers, alkyl esters, alkoxys and alkenyls, $C_6$–$C_{15}$ aryls, halogens, $C_3$–$C_8$ cyclic aliphatics, nitro, aminos (primary and secondary), amidos, cyanos, and hydroxyl, thio, mercapto, sulfo, heterocyclo. The substitution groups are preferably attached to non-fluorinated carbon atoms of $R_1$.

$R_1$ as a $C_1$–$C_{12}$ fluorinated alkyl radical may be straight chained or branched, for example, a fluorinated methyl, ethyl, n-propyl, isopropyl, n-butyl, isobutyl, tert-butyl, n-pentyl, neopentyl, n-hexyl, n-heptyl, n-octyl or 2-ethylhexyl. Any of these groups may be substituted with essentially any conventional organic moiety, for example, methoxy, ethoxy, n-propoxy, isopropoxy, n-butoxy, methanesulphonyl, cyano, bromine or chlorine.

$C_1$–$C_6$ fluorinated alkyl radicals are even more preferred. Examples include fluoromethyl, difluoromethyl, trifluoromethyl, fluoroethyl, difluoroethyl, trifluoroethyl, pentafluoroethyl, perfluoropropyl, perfluorobutyl, perfluoropentyl, or perfluorohexyl. In the most preferred form, $R_1$ is a trifluoromethyl radical.

$R_1$ as a fluorinated $C_3$–$C_{10}$ cycloalkyl radical may be, for example, a fluorinated cyclopropyl, cyclobutyl, cyclopentyl, methylcylcopentyl, cyclohexyl, methylcyclohexyl, dimethylcyclohexyl, cycloheptyl or cyclooctyl. Any of these groups may be substituted by essentially any conventional organic moiety, for example, methoxy, ethoxy, n-propoxy, n-butoxy, methanesulphonyl, cyano, bromine or chlorine.

$R_1$ as a 3–10 ring member fluorinated heterocyclic radical may include known heterocyclic atoms such as N, O and S. Suitable fluorinated heterocycles include, for example, fluorinated pyran, thiophene, pyrrole, furan, pyridine or derivatives thereof.

$R_1$ as a $C_6$–$C_{15}$ fluorinated aryl may be, for example, a fluorinated phenyl, o-tolyl, m-tolyl, p-tolyl, o-xylyl, m-xylyl, p-xylyl, alpha-napthyl, or beta-napthyl. Any of these groups can be substituted with, essentially any conventional organic radical, for example, halogen, $C_1$–$C_4$ alkoxyl or nitro.

$R_1$ as a $C_7$–$C_{20}$ fluorinated aralkyl radical may be, for example, a fluorinated benzyl, 4-methylbenzyl, o-methylbenzyl, p-methylbenzyl, diphenyl-methyl, 2-phenylethyl, 2-phenylpropyl, or 3-phenylpropyl, and preferably a fluorinated $C_7$–$C_9$ aralkyl, especially fluorinated benzyl. Any of these groups may also be substituted with essentially any conventional organic moiety, for example, halogen, $C_1$–$C_4$ alkoxyl or nitro. The halogen, alkoxyl or nitro may be substituted in the aryl portion of the group, or in the alkyl portion of the group. The fluorine may be substituted in either the aryl group or the aryl portion of the aralkyl group to form, for example, a mono-, di-, tetra-, tert- or penta-fluorophenyl group. Alternatively, the fluorine may be substituted in the alkyl portion of the aralkyl group to form, for example, mono-, di- or tetrafluorobenzyl.

The compounds of Formula I may exist in isomeric form. For example, when $R_1$ is $CF_3$—CFH—$CF_2$—, the compounds of Formula I have an asymmetric carbon at the —CFH— position, and consequently, they can exist in the form of different combinations of R- and S-isomeric forms as enantiomers or racemates. In addition, cis and trans geometric isomers may also be present in the subject compounds. All racemic and isomeric forms of the compounds of Formula I, including pure enantiomeric, racemic and geometric isomers and mixtures thereof, are within the scope of the invention.

The compounds of the invention may be made by a number of methods. For example, the fluorinated oxyvinyl ethers of the invention may be made the process are disclosed in the above-referenced U.S. patent application Ser. No. 09/009,110.

Specific examples of fluorinated oxyvinyl ethers of the invention are: $HCF_2(CF_2)_3CH_2O(CH_2)_4OCH=CH_2$; $CF_3CH_2O(CH_2)_4OCH=CH_2$; $HCF_2(CF_2)_5CH_2O(CH_2)_4OCH=CH_2$; $CCl_3CH_2O(CH_2)_2OCH=CH_2$;

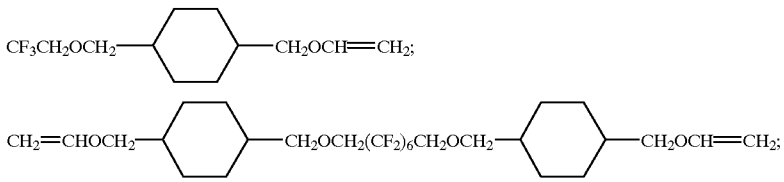

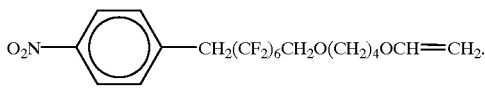

$HOCH_2(CF_2)_6CH_2O(CH_2)_4OCH=CH_2$; $CH_3OCH_2(CF_2)_6CH_2O(CH_2)_4OCH=CH_2$; $HSCH_2(CF_2)CH_2O(CH_2)_4OCH=CH_2$; and

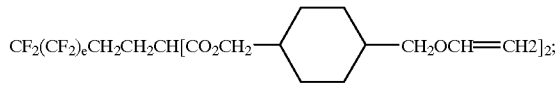

The oxyvinyl ethers of the invention are prepared by the process disclosed in the above-referenced U.S. patent application Ser. No. 09/009,110. Likewise, the fluorinated vinyl ether esters of this invention are prepared by the transesterification reaction disclosed in the above-referenced U.S. patent application Ser. No. 09/009,110.

Examples of the oxyvinyl esters of the present invention are: $CF_3(CF_2)_5CH_2CH_2CH[CO_2(CH_2)_4OCH=CH_2]_2$; $CCl_3(CF_2)_5CH_2CH_2CH[CO_2(CH_2)_4OCH=CH_2]_2$; $CF_3(CF_2)_9CH_2CH_2CH[CO_2(CH_2)_4OCH=CH_2]_2$; $CF_3(CF_2)_7CH_2CH_2CH[CO_2(CH_2)_4OCH=CH_2]_2$; $CF_3(CF_2)_eCH_2CH_2CH[CO_2(CH_2)_4OCH=CH_2]_2$;

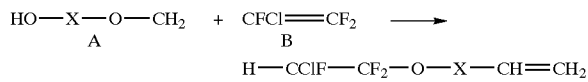

$CF_3(CF_2)_5CH_2CH_2CH[CO_2CH_3][CO_2(CH_2)_4OCH=CH_2]$; $CF_3(CF_2)_7CH_2CH_2CH[CO_2CH_3][CO_2(CH_2)_4OCH=CH_2]$; and $CF_3(CF_2)_9CH_2CH_2CH[CO_2CH_3][CO_2(CH_2)_4OCH=CH_2]$.

The compounds of Formula I in which R is HCFCl—$CF_2$— are prepared by the following reaction scheme:

$$HO-X-O-CH_2 + CFCl=CF_2 \longrightarrow$$
$$\quad\quad A \quad\quad\quad\quad\quad B$$
$$H-CClF-CF_2-O-X-CH=CH_2$$

The compounds of Formula I in which R is $R_1$—CFH—$CF_2$— or $R_1$—CF=CF— are prepared by a similar process in which $R_1$—CF=$CF_2$ is substituted for CFCl=$CF_2$, which is disclosed in parent U.S. patent application Ser. No. 09/218,201. Depending upon process conditions, an additional product may be formed having the formula $R_1$—CHF—$CF_2$—O—X—CH=$CH_2$.

A variety of vinyloxyalcohols are commercially available having the structure of Compound A, including, for example, compounds wherein X is an ethyl or butylene radical (available from Aldrich Chemical Co.); or a cyclohexyldimethyl radical (available from BASF Corp.). Furthermore, many compounds having the structure of Compound A are known in the literature and are obtainable by art-recognized procedures, see, for example, Sukhinin, et al., *Zh. Vses. Khim. O-va.*, 26(3), 344–5 (1981). Compound B is also commercially available from Aldrich Chemical Co.

A number of methods for the preparation of vinyl ethers are known, see Fischer, P. *Enol Ethers-Structure, Synthesis and Reactions*, p. 761–920, in Patai, S., Editor "Chemistry of Ethers, Crown Ethers, Hydroxyl Groups and Their Sulfur Analogues" (Wiley, Chichester, UK (1980). The conversion of Compound A to compounds of Formula I may be accomplished by slight modification of the procedures reported in Bayliff, et al., *J. Chem. Soc. Perkin Trans.* 1, 4, 763–767, (1987) and Kanunyants, et al., *Izv. Akad. Nauk SSSR Otdel. Khim. Nauk,* 282 (1953). The disclosures of these publications are incorporated herein by reference.

In a typical procedure, a mixture of Compound A, an aprotic solvent, and a base is stirred, with slow addition, preferably dropwise, of Compound B. Preferably about 2.0 to 2.5 parts by weight of solvent per part by weight of Compound A is employed. However, those of ordinary skill in the art will understand how to successfully employ higher or lower quantities of solvent. Although the reaction is not inhibited by oxygen, it is preferred to conduct the reaction under a blanket of an inert gas such as, for example, nitrogen.

Suitable aprotic solvents include, for example, acetonitrile, dimethylformamide, and tetrahydrofuran. In a preferred embodiment, the aprotic solvent is acetonitrile.

The amount of base used in the synthesis of compounds of Formula I can range from a catalytic to a stoichiometric amount. Catalytic amounts typically range between about 0.1 to about 20 mole percent relative to the hydroxyvinyl alcohol (Compound A) of Reaction Scheme I. In light of this disclosure, one skilled in the art can readily optimize the amount of base used in the reaction without undue experimentation.

The compounds of Formula I obtained from the aforementioned reaction may be purified by conventional methods known to those skilled in the art. For example, aqueous washes, drying, concentrating under reduced pressure, distillation, and the like may be used.

The compounds of Formula I in which R is $R_1$—[CFCl—$CF_2$—$]_p CH_2$— were prepared by the reaction scheme shown below, in which p is an integer between 1 and 20, inclusive:

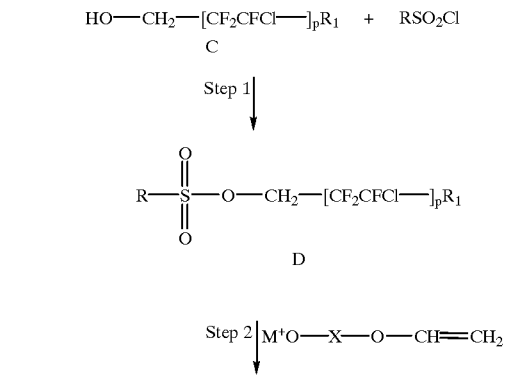

-continued

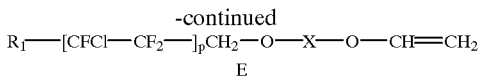

Step 1

The compounds of Formula (C) were prepared by minor modification of the procedure reported by Fikar et al., *Collect. Czech. Chem. Commun.*, 1996, 61, 1215 from methanol and chlorotrifluoroethylene. To a stirred solution of alcohol in a solvent such as THF was added the sulfonyl chloride to afford the intermediate $RSO_3CH_2[CF_2CFCl]_pR_1$ (D) which not isolated but used without further purification for the Step 2 of the reaction. A number of sulfonyl chlorides can be utilized for this reaction, for example, benzenesulfonyl chloride, p-toluenesulfonyl chloride, and the like. In the formula $RSO_2Cl$, R=alkyl or aryl; the preferred R is an aryl, such as phenyl or p-toluyl group.

Step 2

In step 2 the alkoxide anion $[M^+O—X—OCH=CH_2]$ was generated from the vinyloxy alcohol $HO—X—OCH=CH_2$. To a stirred solution of the alcohol in a solvent such as THF was added a base, sodium tert-butoxide. The resulting alkoxide anion was added to the in situ generated $RSO_3CH_2[CF_2CFCl]_pR_1$ (D) in step 1 to afford Compound (E). The thus obtained Compound E was purified by conventional methods of the art, for example, aqueous washes, drying, concentrating under reduced pressure, distillation and the like.

The vinyl monomers of Formula I contain much less hydrogen than conventional photocurable monomers such that their inherent carbon-hydrogen bond absorption is greatly reduced. In addition, the introduction of chlorine or bromine atoms into the molecule can offset the effect of fluorine on the refractive index of the monomer, producing a material with an index of refraction between about 1.40–1.48. As a result, the monomers of the invention may be particularly useful in optical applications in the 1300–1550 nm wavelength region. The monomers are also compatible with both conventional hydrogen-based and highly fluorinated monomers. Because of this compatibility, it becomes possible to fine tune the refractive index and other physical properties of photocurable compositions by mixing these photocurable monomers with the monomers of Formula I, including compounds in which R is $R_1$—CHF—$CF_2$ and $R_1$—CF=CF—.

Accordingly, the curable compositions of the present invention containing the vinyl monomers of Formula I are especially useful in the polymerization of new polymers for a number of optical applications, especially in such high technology areas as optical fibers, optical instruments and equipment, electronics, coatings, laminates, and extruded or molded shapes and articles, for example, for equipment exposed to a corrosive environment such as integrated circuit fabricating equipment. Polymers for such applications may be polymerized from compositions containing vinyl monomers according to Formula I in which R is $R_1$—CFH—$CF_2$— or $R_1$—CF=CF—.

Coatings derived from compounds of the present invention may be applied for example, to capacitors, resistors, and integrated circuits, for the purpose of encapsulating them to protect them from harmful environment or to provide a highly dielectric layer; to plastic sheets or metal foils for the purpose of protecting them from damage or for making laminates; to interior walls of reactors, especially those employed in highly corrosive reactions with concentrated acids or with hydrofluoric acid, to protect them from corrosion; to light-transmissive devices such as optical lenses, prisms, and glazing to impart to them improved abrasion resistance or resistance against damage in corrosive environments; to glass or quartz cores for optical fibers to form a cladding; and recording heads, disks, and tapes, and to components of radio and microwave receiving equipment such as antenna dishes, etc. to protect them from mechanical or environmental damage.

The compounds of the present invention are also characterized by the ability to form coatings that, upon curing, possess unique and useful surface properties including excellent surface wetting and low surface tension prior to curing, and low surface energy, low friction and high slip, low flammability, high chemical resistance, and excellent moisture resistance after curing. It is believed that the desirable surface properties are the result of the fluorine-containing moieties migrating to the surface of cured coatings of the monomer compound, which contribute protective properties to the coating, as well. The fluorine-containing moieties also contribute surfactant-like qualities to the monomer compound that provide better flow, leveling and wetting, which is desirable for coating and ink compositions. Therefore, in addition to optical applications, the curable compositions of the invention containing the vinyl monomer of Formula I, including the monomers in which R is $R_1$—CHF—$CF_2$— or $R_1$—CF=CF—, find utility in numerous other areas, including, but not limited to, coatings, inks, photoresists, films, fibers, adhesives, insulators, laminates, elastomers, foams, molds and release coatings.

The present invention thus also provides for a curable composition comprising at least one compound of Formula I. When only a compound of Formula I is present, the resulting polymer is a homopolymer. When other monomers are present, a copolymer is produced.

The compositions may be curable by application of heat energy or exposure to actinic radiation. Initiator compounds may be employed. Microwave radiation may be used to apply heat to the composition. The compositions may also be catalytically cured with or without application of heat or exposure to actinic radiation by using an effective amount of a Lewis Acid catalyst, such as $BF_3$. For example, the vinyl ether compounds of the present invention may be incorporated into sulfonic acid-cured epoxy maleate systems, which then cure at 300° F. within 15 seconds. Compounds of Formula I in which R is $R_1$—CHF—$CF_2$— or $R_1$—CF=CF— are included among the compounds that may be cured by using a Lewis Acid catalyst.

For purposes of the present invention, compositions that are curable by exposure to actinic radiation are defined as being "photocurable." Suitable sources of actinic radiation include light in the visible, ultraviolet or infrared regions of the spectrum, as well electron beam, ion or neutron beam or X-ray radiation. Actinic radiation may be in the form of incoherent light or coherent light such as light from a laser.

In photocuring processes, the actinic radiation is used to initiate addition polymerization of the vinyl ether compounds. Initiation of addition polymerization by actinic radiation is greatly enhanced by the use of photoinitiators. A unique feature of the present invention is that either free-radical or cationic photoinitiators may be employed. Free-radical photoinitiators propagate addition polymerization of terminal ethylenically unsaturated groups of the curable components in the compositions of the present inventions. Suitable free-radical photoinitiator compounds may be readily selected by those skilled in the art, and include, for example, DAROCUR 1173, DAROCUR 4265, IRGACURE 184, IRGACURE 261, IRGACURE 369, IRGACURE 500, IRGACURE 651, IRGACURE 784, IRGACURE 907, IRGACURE 1700, IRGACURE 2959, IRGACURE 1800, IRGACURE 1850, IRGACURE 819, AND IRGACURE 1300 (each commercially available from Ciba Specialty Chemicals) and GE-PI (commercially available from GE Corporation).

Cationic photoinitiator compounds propagate the addition polymerization of vinyl ether compounds, which include the curable components of the compositions of the present invention. Cationic photoinitiators undergo photolysis under the influence of actinic radiation, resulting in the formation of Lewis acids that, in turn, propagate the addition polymerization. Suitable cationic photoinitiator compounds may also be readily selected by those of skilled in the art, and include, for example, the onium salts conventionally employed as cationic photoinitiators, including triarylsulfonium and triaryliodonium salts.

The free radical or cationic initiator is present in an amount sufficient to effect polymerization of the curable component. The free radical or cationic initiator may comprise from about 0.01 to about 10% by weight, preferably from about 0.1 to about 6% by weight, and more preferably from about 0.5 to about 4% by weight of the total curable composition. Photocurable compositions contain an amount of a free radical or cationic photoinitiator within the foregoing ranges that is sufficient to effect photopolymerization of the photocurable component upon exposure to sufficient actinic radiation. Compounds of Formula I in which R is $R_1$—CHF—$CF_2$— or $R_1$—CF=CF—are included among the compounds that may be photocured using a cationic photoinitiator.

The amount of curable component in the curable compositions may vary widely. Depending upon the application, the component is present in an amount of from about 0.01 to about 99% by weight of the overall composition. For applications which rely upon physical properties of the curable compound other than surface properties, the curable component is preferably present in the curable composition at a level of at least about 35% by weight. In a preferred embodiment, the curable component is present in an amount of from about 80 to about 99% by weight, and, more preferably, from about 95 to about 99% by weight of the overall composition. Photocurable compositions contain an amount of the curable component within the foregoing ranges that is sufficient to photocure and provide image differentiation upon exposure to sufficient actinic radiation.

For applications which rely upon the ability of the curable component to modify the surface properties of other polymer systems, the curable component is preferably present in the curable composition at a level between about 0.10% and about 2.00% by weight. A level of about 0.50% by weight is preferred. For this aspect of the present invention, R is also $R_1$—CFH—$CF_2$— and $R_1$—CF=CF—.

In addition to the compound of Formula I, other curable compounds which are known in the art may be incorporated into the curable compositions of the present invention. These compounds include monomers, oligomers and polymers containing at least one terminal ethylenically unsaturated group and being capable of forming a high molecular weight polymer by free radical initiated, chain propagating addition polymerization. Suitable monomers include, but are not limited to, ethers, esters and partial esters of: acrylic and methacrylic acids; aromatic and aliphatic polyols containing from about 2 to about 30 carbon atoms; and cycloaliphatic polyols containing from about 5 to about 6 ring carbon atoms. Specific examples of compounds within these classes are: ethylene glycol diacrylate and dimethacrylate, diethylene glycol diacrylate and dimethacrylate, triethylene glycol diacrylate and dimethacrylate, hexane diacrylate and dimethacrylate, trimethylolpropane triacrylate and trimethacrylate, dipentaerythritol pentaacrylate, pentaerythrytol triacrylate, pentaerythrytol tetraacrylate and trimethacrylate, alkoxylated bisphenol-A diacrylates and dimethacrylates (e.g., ethoxylated bisphenol-A diacrylate and dimethacrylate and propoxylated bisphenol-A diacrylates and dimethacrylates), alkoxylated hexafluorobiphenol-A diacrylates and dimethacrylates and mixtures of the above compounds. Preferred monomers include multifunctional aryl acrylates and methacrylates. Preferred arylacrylate monomers include di-, tri- and tetraacrylates and methacrylates based on the bisphenol-A structure. More preferred arylacrylate monomers are alkoxylated bisphenol-A diacrylates and dimethacrylates such as ethoxylated bisphenol-A diacrylates and dimethacrylates, and ethoxylated hexafluoro-bisphenol-A diacrylates and dimethacrylates.

Suitable oligomers include, but are not limited to, epoxy acrylate oligomers, aliphatic and aromatic urethane acrylate oligomers, polyester acrylate oligomers, and acrylated acrylic oligomers. Epoxy acrylate oligomers (such as Ebecryl 600 by UCB) are preferred.

Suitable polymers include, but are not limited to, acrylated polyvinyl alcohols, polyester acrylates and methacrylates, acrylated and methacrylated styrene-maleic acid copolymers. Acrylated styrene-maleic acid copolymers are preferred.

Other curable compounds known in the art that may be incorporated into the curable compositions of the present invention include monomers, oligomers and polymers containing at least one terminal epoxide ring and being capable of forming a high molecular weight polymer by cationic ring-opening polymerization. Suitable epoxide-functional compounds include aromatic, aliphatic and mixed aromatic and aliphatic epoxy acrylates and polymers and oligomers thereof, epoxy novolaic polymers and oligomers, and cycloaliphatic epoxies, and polymers and oligomers thereof. Epoxy acrylate oligomers are preferred, including acrylated diglycidyl ethers of bisphenol-A, such as Ebecryl 600. Oligomers of diglycidyl ethers of bisphenol-A are also preferred.

Significantly, the vinyl ether compounds of the present invention polymerize with the ethylenically unsaturated and epoxide-functional compounds, either by free radical initiated chain propagation addition polymerization with the ethylenically unsaturated compounds, or, with cationic photoinitiators, by a combination of ring-opening polymerization of epoxide group and addition polymerization of vinyl ethers.

When other ethylenically unsaturated or epoxide-functional monomers, oligomers or polymers are employed, the weight ratio of the monomer compound of Formula I to the ethylenically unsaturated or epoxide-functional compounds may vary from about 0.1:99.9 to about 99:1, preferably from about 1:9 to about 9:1, and more preferably from about 25:75 to about 75:25.

Various optional additives may also be added to the curable compositions of the invention depending upon the application in which they are to be used. Examples of these optional additives include antioxidants, photostabilizers, volume expanders, fillers (e.g., silica and glass spheres), dyes, free radical scavengers, contrast enhancers and UV absorbers.

Antioxidants include such compounds as phenols and particularly hindered phenols including Irganox 1010 from Ciba Specialty Chemicals; sulfides; organoboron compounds; organophosphorus compounds; and N, N'-hexamethylene-bis(3,5-di-tert-(butyl-4-hydroxy-hydrocinnamamide)) available from Ciba Specialty Chemicals under the trade name Irganox 1098. Photostabilizers and more particularly hindered amine light stabilizers include, but are not limited to, poly[(6-hexamethylene)2,2,6,6-tetramethyl-4-piperidinyl)imino)] available from Cytech Industries under the trade name Cyasorb UV3346. Volume expanding compounds include such materials as the spiral monomers known Bailey's monomer. Suitable dyes include methylene green and methylene blue. Suitable free radical scavengers include oxygen, hindered amine light stabilizers, hindered phenols, and 2,2,6,6-tetramethyl-1-piperidinyloxy free radical (TEMPO). Suitable contrast enhancers include other free radical scavengers. UV absorbers include benzotriazoles and hydroxybenzophenone.

The additives may be used in amounts, based on the total composition weight, of from about 0 to about 6%, and preferably from about 0.1% to about 1%. Preferably all components of the curable composition are in admixture with one another, and, preferably, in a substantially uniform admixture.

The photocurable compositions of the invention can be used in the formation of the light transmissive element of an optical device. Examples of such devices are planar optical slab waveguides, channel optical waveguides, ribbed waveguides, optical couplers, routers, combiners and splitters. The photocurable composition of the invention can also be used in the formation of negative working photoresists and other lithographic elements such as printing plates. In a preferred embodiment, the photocurable composition is used for producing a waveguide comprising a substrate containing a light transmissive element. Such waveguides are formed by applying a film of the photocurable composition of the invention to the surface of a suitable substrate. The film may be formed by any method known in the art, such as spin coating, dip coating, slot coating, roller coating and evaporation.

The substrate may be any material on which it is desired to establish a waveguide including semiconductor materials such as silicon, silicon oxide, gallium arsenide, polymers and compound materials. In the event the light transmissive region on the substrate is to be made from a photocurable material which has an index of refraction which is lower than that of the substrate, an intermediate buffer layer possessing an index of refraction which is lower than the substrate must be applied to the substrate before the photocurable composition is added. Otherwise, the light loss in the waveguide will be unacceptable. Suitable buffers are made from semiconductor oxides, lower refractive index polymers or spin on silicon dioxide glass materials.

Once a film of the photocurable composition is applied to the substrate, actinic radiation is directed onto the film in order to delineate the light transmissive region. That is, the position and dimensions of the light transmissive device are determined by the pattern of the actinic radiation upon the surface of the film on the substrate. The photopolymers of the invention are conventionally prepared by exposing the photocurable composition to sufficient actinic radiation. For purposes of this invention, "sufficient actinic radiation" means light energy of the required wavelength, intensity and duration to produce the desired degree of polymerization action in the photocurable composition.

Sources of actinic light, exposure procedures, times, wavelengths and intensities may vary widely depending upon the desired degree of polymerization, the index of refraction of the photopolymer, and other factors known to those of ordinary skill in the art. The selection and optimization of these factors are well known to those skilled in the art.

Preferably the photochemical excitation is carried out with relatively short wavelengths (or high energy) radiation so that exposure to radiation normally encountered before processing (e.g., room lights) will not prematurely polymerize the polymerizable material. The energy necessary to polymerize the photocurable compositions of the invention generally ranges from about 5 mW/cm$^2$ to about 200 mW/cm$^2$ with typical exposure times ranging from 0.1 second to about 5 minutes.

After the photocurable composition has been polymerized to form a predetermined pattern on the surface of the substrate, the pattern is then developed to remove the non-image areas. Any conventional development method can be used such as flushing the non-irradiated composition with a solvent. Suitable solvents include polar solvents, such as alcohols and ketones. The most preferred solvents are acetone, methanol, tetrahydrofuran and ethyl acetate.

While the preferred embodiment of the invention involves photocuring the photocurable composition, as noted above, one skilled in the art will appreciate that many variations of the method within the scope of the claims are possible depending upon the nature of the curable composition. For example, the composition may be heat-cured in an oven or through another heat source such as microwave radiation. Alternately, the composition may be cured using a Lewis Acid catalyst. Depending upon the particular use, the photocurable composition may be partially cured before application to a surface and subsequently fully cured.

The present invention also provides for a polymer comprising one or more vinyl ether repeating units, alone or with other repeating units, wherein the vinyl ether repeating units have the formula:

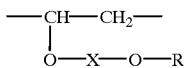

wherein X and R are the same as described above with respect to Formula I. The vinyl ether repeating units are formed from the polymerization of compounds of Formula I.

In one embodiment, the polymer of the present invention may be a homopolymer comprising only a single vinyl ether repeating unit of Formula I, or the polymer may comprise two or more vinyl ether repeating units derived from different compounds of Formula I. In an alternative embodiment, the polymer of the present invention may include one or more second repeating units derived from other monomers, oligomers, or polymer compounds that have been copolymerized with a vinyl ether compound of the present invention, and which are disclosed above as additional curable compounds that may be included in the curable compositions of the present invention. The polymer of the present invention can contain as little as 0.01% by weight of the vinyl ether repeating unit or amounts in excess of 90% by weight.

EXAMPLES

In order that the invention may be more readily understood, reference is made to the following examples which are intended to be illustrative of the invention, but are not intended to be limiting in scope.

Example 1

Preparation of 5H-Octafluoropentane-oxybutylvinyl Ether, HCF$_2$(CF$_2$)$_3$CH$_2$O(CH$_2$)$_4$OCH=CH$_2$ Octafluoropentanol (487.4 g, 2.1 mol) was added dropwise to a suspension of sodium t-butoxide (203.8 g, 2.12 mol) in 500 g of tetrahydrofuran at a rate to maintain the reaction temperature at ≦25° C. After the addition was complete, 12.0 mol of butyl vinylether benzene sulfonate, prepared as disclosed by Example 1 of U.S. patent application Ser. No. 09/009,110, was added and the reaction heated to 80° C. for 8 hours. The solvent was then removed by distillation and the resulting solid dissolved in 3L of water. The lower organic phase was separated and the product distilled at 54–58° C./0.4 mm to yield 508.3 g (77%).

Example 2

Preparation of Trifluoroethylcyleohexyltetrafluoroethyl oxybutylvinyl Ether,

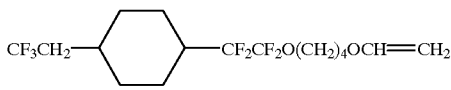

This material is prepared as described in Example 1 except that 9 mol of 2-[4-(2,2,2,-trifluoroethyl) cyclohexy] tetrafluoroethanol is used. Yield of the product which was distilled at 35–40° C./0.2 mm was 1488.11 g (84%).

Example 3

Preparation of 2,4,6-Trifluorobenzyl-oxybutylvinyl Ether

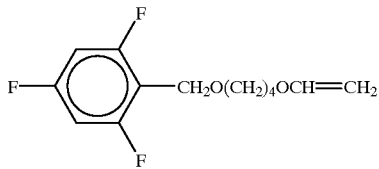

This compound is prepared as described in Example 1 except that 2.12 mol of 2,4,6-trifluorobenzyl alcohol is used in the reaction sequence.

Example 4

Preparation of 3-(perfluorooctyl) Propanedioic Acid, di(butylvinyl Ether) diester, $CF_3(CF_2)_5CH_2CH_2CH[CO_2(CH_2)_4OCH=CH_2]_2$ 3-(Perfluorooctyl)propanedioic acid, dimethyl diester (85 g, 0.178 mol) (prepared as disclosed by Example 11 of U.S. patent application Ser. No. 09/009,110), hydroxy-butylvinyl ether (62 g, 0.52 mol) and titanium tetraisopropoxide (0.081 g, $2.8 \times 10^{-4}$ mol) were reacted at 100–112° C./50 mm to effect the transesterification reaction. The product was isolated by vacuum distillation. The fraction boiling at 96–100° C./0.2 mm was identified as the product fraction. Yield= 131.5 g (97%).

Example 5

Preparation of

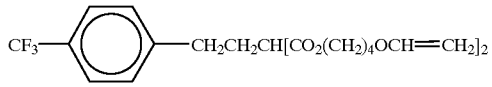

p-Trifluoromethylphenyl propanedioic acid dimethyl ester produced according to the process described in Example 11 of U.S. patent application Ser. No. 09/009,110 (0.15 mol) is reacted with hydroxybutylvinyl ether (51 g, 0.45 mol) and titanium tetraisopropoxide (0.068 g, $2.4 \times 10^{-4}$ mol) as described in Example 5. The product is isolated by distillation at 160° C./0.1 mm.

Example 6

Preparation of

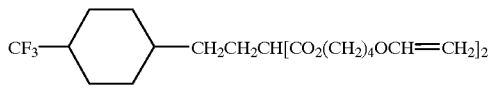

3-[4-Trifluoromethyl]cyclohexyl propanedioic acid dimethyl ester produced according to the process described in Example 11 of U.S. patent application Ser. No. 09/009,110 (0.398 mol) is reacted with hydroxybutylvinyl ether (138.5 g, 1.19 mol) and titanium tetraisopropoxide (0.181 g, $6.3 \times 10^{-4}$ mol) as described in Example 5. The product is isolated by distillation at 140–145° C./0.2 mm.

Example 7

This example demonstrates the surface modification properties of the vinylether compounds of the present invention. Acrylate and vinyl ether polymers were made by UV polymerization of acrylate and vinyl ether monomers. Such polymers were prepared by homopolymerization without additives, and with non-reactive fluorochemical surfactant additive and by copolymerization with a compound of the present invention.

The resulting polymers were compared on the basis of surface fluorine, surface tension, blocking, release, bulk tensile properties and elongation. The results are shown in Table I.

Column 1 of the table gives the major resin composition in the polymer being tested.

The "acrylate" polymer comprised a cured mixture of 80 weight % aliphatic urethane diacrylate oligomer, UCB Corporation trademark "Ebecryl 8804"; 20 weight % hexanediol diacrylate, and 2 parts per hundred (pph) of α-α-dimethoxyphenylacetophenone, free radical photocuring initiator, available under Ciba Specialty Chemical trademark "Irgacure 651", plus additives shown in Column 2 of the table.

The acrylate polymer was UV cured under nitrogen. At least about 200 millijoules (mJ)/cm$^{-2}$ of UV exposure from a medium pressure mercury lamp was required for complete cure.

"FAVE" means FAVE 4101, a fluoroalkyl vinyl ether of the invention.

FAVE alone was cured using sulfonium hexafluoroanitmonate photoinitiator, available from GE Corporation under the trademark "GE-PI." Radiation exposure was about 400 mJ/cm$^2$ to cure.

"Vinyl Ether" in Column 1 is a cured 50/50 combination of polyester divinyl ether oligomer, available from Allied-Signal Inc. under the trademark "VEX 1221" and 1,2-benzene carboxylic acid bis([4-(ethenyloxy)butyl] ester, available from AlliedSignal, Inc. under the trademark VE4010D. 0.5 pph of triaryl sulfonium salt of hexafluoro antimonate cationic photoinitiator was used. The photoinitiator is available from Sartomer Company, Inc. under the trademark CD1010. The vinyl ether was completely cured using about 400 mJ/cm$^2$ of UV radiation.

As shown in Column 2 of the table, there was either no additive, FLUORAD FC430 fluorochemical surfactant additive, FLUORAD FC 171 fluorochemical surfactant additive or FAVE copolymerized additive of the invention. FLUORAD is a trademark of 3M Corporation for water-soluble non-ionic fluoroaliphatic surfactant.

Column 3 of the table shows percent atomic fluorine at the top surface (TFS) by photoelectron spectroscopy based upon the total carbon, nitrogen, oxygen, fluorine and silicon. Column 4 shows percent atomic fluorine at the bottom surface (BFS).

Column 5 shows percent top surface atomic fluorine after 20+ rubs with methyl ethyl ketone (MEK) for the acrylate and 100% FAVE polymer coatings and 4+ rubs with MEK for the vinyl ether polymer coatings. Column 6 shows percent top surface atomic fluorine after being postcured at 80° C. for 15 minutes and after 20+ rubs with methyl ethyl ketone for polyacrylate and 4+ rubs for polyvinyl ether.

Column 7 shows surface tension in dynes/cm. Column 8 shows block separation force between top surfaces using 44 g per square inch block forming pressure. Block separation force is force in grams to peel back a blocked section of one half inch width at 1.5 inches per minute.

Column 9 shows force of release of adhesive tape from the top surface at 12 inches per minute. The tape used was 3M Corporation 810 adhesive tape. Columns 10 and 11 how tensile strength using the Youngs Modulus in Ksi. "Ksi"= 1000 psi and stretch characteristics using percent elongation.

This example illustrates the resulting effect on surface energy by adding various load levels of the fluoroalkyl vinyl ethers of this invention into standard acrylate formulations and into standard vinyl ether formulations used by those in the industry. As can be seen, the addition of the fluoroalkyl vinyl ethers has a dramatic effect in reducing the surface tension in both the neat liquid and the cured film at even the 0.1 weight % level. The lower surface tension in the liquid state as compared to the patent formulation indicates that these fluids will have an improved surface wetting property. Similarly, the decrease in surface energy of the polymerized film indicates that these materials will exhibit low surface tension, low friction and non-stick surfaces.

This example also demonstrates the unique manner in which the vinylether compounds of the present invention predominantly modify the top surface of a film or coating. The atomic fluorine levels are significantly higher for the top, rather than the bottom, surface of a coating containing FAVE. The fluorinated surfactant additive compounds of the prior art modify both the top and bottom surfaces of a film or coating. This detracts from the adhesion of a coating to the underlying substrate.

This example further demonstrates the non-fugitive properties of the vinyl ethers of this invention in acrylate and vinyl ether polymer compositions. It compares the vinyl ethers of the invention to commercially available fluorinated surfactants used in the art. As can be observed, after performing the industry standard test of MEK double rubs, polymerized films containing the fluorinated surfactant additives significantly decrease in percent surface content of fluorine as compared to the fluorinated materials of this invention. While surface fluorine content increases for surfactant additive modified compounds upon curing, the surfactant is still fugitive and these values are expected to decrease. This substantiates the non-fugitive nature of the materials of the invention as compared to current art materials, as well as demonstrating that materials formulated and polymerized with the fluorinated ethers will exhibit extended wear performance, resistance and the like. The higher surface fluorine content of compounds of the invention, coupled with its steady state value as compared to the decreasing value observed with the fluorinated surfactant series of fluorinated additives, demonstrate improvements over prior art technology.

The results of this example further demonstrate that the oxyvinyl ethers of the invention can be used both in acrylate and vinyl ether based polymers. Materials of these compositions will impart improved wear, temperature resistance and chemical resistance, just to indicate a few enhanced properties. Such properties can thus be enhanced by use of the compounds of the invention in many areas such as release coatings, protective coatings, plastics, inks, moldings, adhesives and optical devices.

TABLE I

CORRELATION OF SURFACE FLUORINE WITH SURFACE TENSION, BLOCKING, RELEASE, BULK TENSILE PROPERTIES AND ELONGATION

| Major Resin | Additive | TFS Atomic Fluorine | BFS Atomic Fluorine | TFS after MEK | TFS after MEK Postcure | Surface Tension of Cured Film Top | Surface Tension of Liquid | Top to Top Blocking Grams | Release Grams | Tensile Youngs Modulus (Ksi) | % Elongation at Break |
|---|---|---|---|---|---|---|---|---|---|---|---|
| Example 19 FAVE | none | 34.42 | 31.6 | 35.42 | 33.3 | | | | | | |
| Acrylate 100% | none | 0 | 0 | 0 | 0 | 42 | 51 | 5 | 626 | 56 | 31 |
| Acrylate | 0.1 pph Example 19 FAVE | 8 | 0 | 6.1 | 7.1 | 32 | 46.9 | 2.6 | 611 | | |
| Acrylate | 0.5 pph Example 19 FAVE | 15.3 | 0.6 | 13.9 | 14 | <30 | 42.2 | 1.4 | 350 | 54 | 31 |
| Acrylate | 0.1 pph FC-430 | 1.7 | 0.5 | 0.7 | 1.1 | 38 | 41.4 | 3.9 | 560 | | |
| Acrylate | 0.5 pph FC-430 | 6.7 | 0.69 | 1.8 | 5.5 | 36 | 35.5 | 2.5 | 465 | 51 | 34 |

TABLE I-continued

CORRELATION OF SURFACE FLUORINE WITH SURFACE TENSION, BLOCKING, RELEASE, BULK TENSILE PROPERTIES AND ELONGATION

| Major Resin | Additive | TFS Atomic Fluorine | BFS Atomic Fluorine | TFS after MEK | TFS after MEK Postcure | Surface Tension of Cured Film Top | Surface Tension of Liquid | Top to Top Blocking Grams | Release Grams | Tensile Youngs Modulus (Ksi) | % Elongation at Break |
|---|---|---|---|---|---|---|---|---|---|---|---|
| Acrylate | 0.1 pph FC-171 | 9.8 | 9.3 | 4.1 | 8.5 | 36 | 37.4 | 2.7 | 673 | | |
| Acrylate | 0.5 pph FC-171 | 15.6 | 11.4 | 10.9 | 16.9 | 34 | 32.6 | 1.4 | 675 | 47 | 29 |
| Acrylate | 0.5 pph Example 16 FAVE | 9 | 0.3 | 7.5 | 7.9 | 30 | 40.2 | 2.3 | 493 | 45 | 40 |
| Acrylate | 0.5 pph Example 8 FAVE | 0.5 | 0.1 | 0.2 | 0.3 | 42 | 41.7 | 4.1 | 608 | 43 | 37 |
| Vinyl Ether | None | 0 | 0 | 0 | 0 | 744 | 36.6 | 345 | 611 | 115.7 | 30.3 |
| Vinyl Ether | 0.5 pph FC-430 | 9.83 | 1.47 | 2.67 | 3.36 | 34 | 30 | 2.3 | 388 | 153.2 | 14.3 |
| Vinyl Ether | 0.5 pph FC-171 | 12.95 | 1.12 | 1.59 | 4.6 | 34 | 29.3 | 3.2 | 604 | 141.2 | 22.2 |
| Vinyl Ether | 0.5 pph Example 19 FAVE | 17.2 | 0.2 | 15.9 | 17.2 | <30 | 36 | | | | |
| Vinyl Ether | 1.0 pph Example 19 FAVE | 21.74 | 0.54 | 20.2 | 20.81 | <30 | 28 | 2.7 | 242 | 134.7 | 26.2 |
| Vinyl Ether | 2.5 pph Example 19 FAVE | 25.65 | 1.23 | 24.63 | 25.31 | <30 | 26.3 | 0.86 | 196 | 131.7 | 25.2 |
| Vinyl Ether | 5 pph Example 19 FAVE | 27.85 | 1.96 | 28.57 | 29.89 | <30 | 25.2 | 1.0 | 160 | 136.8 | 24.4 |

Example 8

This example demonstrates the surface modification properties of the vinylether compounds of the present invention in epoxy coatings. Acrylate and epoxy polymers were made by UV polymerization of acrylate and epoxy monomers. Polymers were also made by UV copolymerizations of various combinations of vinyl ether, epoxy and acrylate monomers. The polymers were prepared without additives, and by copolymerization and terpolymerization with a compound of the present invention, FAVE 4101.

The formulations that were tested are shown in Table II, with the amounts listed being in parts per hundred (pph):

TABLE II

| | A | B | C | D | K | F | G | H |
|---|---|---|---|---|---|---|---|---|
| VE4010 | 40 | 40 | 20 | 20 | — | — | — | — |
| UVR6110 | 45 | — | — | — | 45 | 66.6 | — | 100 |
| Tone0301 | 15 | — | — | — | 15 | 33.3 | — | — |
| DER 331 | — | 60 | — | — | — | — | 100 | — |
| Ebecryl 8804 | — | — | 80 | — | — | — | — | — |

TABLE II-continued

| | A | B | C | D | K | F | G | H |
|---|---|---|---|---|---|---|---|---|
| HDODA | — | — | — | — | 40 | — | — | — |
| CD 1010 | 0.5 | — | — | — | 1 | 0.5 | 0.5 | 0.5 |
| 1651 | — | 2 | 2 | 2 | 2 | — | — | — |

UVR 6110 is a cycloaliphatic epoxide manufactured by Union Carbide. Tone 0301 is a polyester polyol oligomer of polycaprolactone, also manufactured by Union Carbide. DER 331 is a diglycidyl ether of bisphenol-A manufactured by Dow Chemical. Ebecryl 8804 is an aliphatic urethane diacrylate oligomer manufactured by UCB Corporation. SR 349 is an ethoxylated bisphenol-A diacrylate oligomer manufactured by Sartomer. HDODA is a hexanediol diacrylate oligomer.

The resulting polymers were compared on the basis of surface tension and release as a function of the amount of the compound of the present invention present in the polymer. The results are shown in Table III.

TABLE III

| Composition | Cure dose mJ/cm$^2$ | Surface tension | Release (g) | FAVE LEVEL Surface Tension before and after 4 MEK rubs + release data | | | | | | | |
|---|---|---|---|---|---|---|---|---|---|---|---|
| | | | | 0.025 pph | 0.05 pph | 0.1 pph | 0.25 pph | 0.5 pph | 1 pph | 2 pph | 5 pph |
| A | 3200 | 40 | 555.7 | 38/38 563 | 36–38/39 572 | 34/34 528 | <30/<30 441 | <30/<30 355 | <30/<30 334 | <30 260.7 | <30 234.2 |

TABLE III-continued

FAVE LEVEL

| Composition | Cure dose mJ/cm² | Surface tension | Release (g) | Surface Tension before and after 4 MEK rubs + release data | | | | | | | |
|---|---|---|---|---|---|---|---|---|---|---|---|
| | | | | 0.025 pph | 0.05 pph | 0.1 pph | 0.25 pph | 0.5 pph | 1 pph | 2 pph | 5 pph |
| B | 1600 | 40 | 565.2 | 40/38 473 | 36/36 | 34/34 422 | <30/<30 313 | <30/<30 260 | <30/<30 196 | <30 160.8 | <30 142.8 |
| C | 400 | 40 | 528.9 565 | | | 36/36 543 | 34/34 530 | 32/32 497 | <30/<30 433 | <30 419.3 | <30 390.9 |
| D | 400 | 40–42 | 543.4 | 38/36 578 | 34–36/36 478 | 32–34/34 478 | <30/<30 388 | <30/<30 307 | <30/<30 284 | <30 254.1 | <30 247.9 |
| E | 400 | >44 | 546 | | | | 38/38 495 | 34–36/34 476 | 34/34 359 | 32/32 3400 | 32 347.6 | 30 314.8 |
| F | 3000 | 42–44 | 558 | | 36/36 486 | 32–34/34 394 | | <30/<30 292 | <30/<30 276 | <30 276 | |
| G | 1600 | 42 | 696 | | 34/34 617 | <30/<30 535 | | <30/<30 517 | <30/<30 417 | <30 387.9 | |
| H | 4000 | 40–42 | 581.6 | | 36–38/36 | 34/36 | <30/<30 | <30/<30 | <30 267.5 | | |

Column 1 of the table lists the base resin composition. Column 2 of the table lists the UV exposure from a medium pressure mercury lamp employed to cure the composition.

Column 3 shows surface tension in dynes/cm. Column 4 shows force of release of adhesive tape from the top surface at 12 inches per minute. Columns 5–12 show surface tension and release data for compositions copolymerized and terpolymerized with a fluoroalkyl vinyl ether compound of the present invention. The surface tension is shown both before and after 4 rubs of the polymer coating with methyl ethyl ketone.

This example illustrates the resulting effect on surface energy by adding various low levels of fluoroalkyl vinyl ethers into standard acrylate, epoxy, epoxy/acrylate, epoxy/vinylether and vinylether/acrylate formulations used by those in the industry. Again, the addition of the fluoroalkyl vinylethers has a dramatic effect in reducing the surface tension and force of release in the cured film at even the 0.1 weight % level. The decrease in surface energy of the polymerized films indicates that the films possess low surface tension, low friction and non-stick surfaces. The surface energy of the polymerized film does not change following the industry standard MEK rub test, once again demonstrating the non-fugitive properties of the fluoroalkyl vinyl ethers of this invention in polymer compositions.

The results of this example demonstrate that the oxyvinyl ethers of the invention can also be used in epoxy based polymers.

Example 9

Preparation of 2-Chloro-1,1,2-trifluoro-1-(2-vinyloxyethoxy)ethane HClFC—CF$_2$—O—CH$_2$CH$_2$—OCH=CH$_2$ Chlorotrifluoroethylene CFCl=CF$_2$ (681 g, 4.45 mol) was added dropwise via dry ice condenser to a mechanically stirred mixture of ethyleneglycolvinyl ether (400 g, 4.54 mol) acetonitrile (800 mL) and Cs$_2$CO$_3$ (30 g, 92 mmol) at ~0° C. under N$_2$, over a period of ~3 hours. The reaction flask was placed in an ice bath to moderate the exothermic reaction during the addition of CFCl=CF$_2$. After complete addition of the CFCl=CF$_2$, the reaction mixture was stirred for an additional hour at room temperature and filtered. The filtrate was poured into 2 L water and mixed well. The lower organic layer formed was separated, washed with water (3×300 mL), concentrated under reduced pressure (~1 mmHg), and distilled to afford 755 g (yield=81%) of a colorless liquid; B.P.=33–35° C./1.5 mmHg; refractive index 1.392 at 24.2° C.; GC/MS (EI mode): m/z at 204 for M⁺; $^{19}$F and $^1$H NMR spectral data are consistent with the structure.

Example 10

Preparation of 2-Chloro-1,1,2-trifluoro-1-(2-vinyloxybutoxy) ethane HClFC—CF$_2$OCH$_2$CH$_2$CH$_2$CH$_2$OCH=CH$_2$ Chlorotrifluoroethylene CFCl=CF$_2$ (399 g, 3.43 mole) was added dropwise via dry ice condenser to a mechanically stirred mixture of 1,4-butanediol vinyl ether (400 g, 3.45 mol), acetonitrile (800 mL), Cs$_2$CO$_3$ (33.8 g, 102 mmol) at ~0° C. to room temperature under N$_2$, over a period of ~2–3 hours. The reaction flask was placed in an ice bath to moderate the exothermic reaction during the addition of CFCl=CF$_2$. After the complete addition of CFCl=CF$_2$, the reaction mixture was stirred for an additional hour at ambient temperature and filtered. The filtrate was poured into 2 L water and mixed well. The lower organic layer formed was separated, washed with water (3×300 mL), concentrated under reduced pressure (~1 mmHg) and distilled to afford 585 g (yield=74%) of a colorless liquid; B.P.=52–55° C./1.2 mmHg; refractive index 1.404 at 24.2° C.; GC/MS (EI mode): m/z at 232 for M⁺; $^{19}$F and $^1$H NMR spectral data are consistent with the structure.

Example 11

Preparation of 2-Chloro-1,1,2-trifluoro-1-{[4-(vinyloxymethyl)cyclohexyl]methoxy}propane

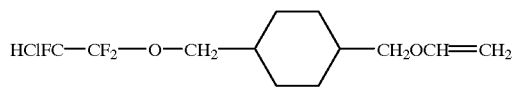

Into a 450 mL capacity PARR® reactor, 1,.4-cyclohexanedimethanol vinyl ether (50 g, 294 mmol), acetonitrile (100 mL), and Cs$_2$CO$_3$ (2 g, 6 mmol) were added. The PARR® reactor was cooled to ~30° C., partially evacuated and chlorotrifluoroethylene (34 g, 294 mmol) was condensed and the resultant mixture was heated at ~50–60° C with stirring for 3 hours. After this, the PARR® reactor was cooled to room temperature, vented in the fume hood and the reaction mixture was poured into ~150 mL water and the lower layer containing the crude product separated, and was concentrated under reduced pressure 0.05 mmHg) at 25–30° C. to afford the desired product as a colorless viscous liquid (49 g, 58% yield) which is a mixture of cis/trans isomers in the ratio 73:18; refractive index of 1.415 at 23.7° C.; GC/MS (EI mode): m/z at 286 for M$^+$; $^{19}$F and $^1$H NMR spectral data are consistent with the structure.

Example 12

Preparation of H[ClFC—CF$_2$]$_n$CH$_2$OH from Methanol and Chlorotrifluoroethylene (n=1, 2, 3, 4 . . . )

Chlorotrifluoroethylene (50 g, 0.43 mmol) was added (in ~5 hours) dropwise via dry ice/isopropyl alcohol condenser, to a stirred mixture of CH$_3$OH (200 g, 6.25 mol) and ditertiarybutylperoxide (7.9 g, 54 mmol) in a quartz reaction vessel subjected to UV radiation (254 nm). After complete addition of CTFE, the reaction mixture was stirred for an additional hour and concentrated under reduced pressure (~20 to 5 mmHg/70° C.). GC of this material indicated H[ClFC—CF$_2$]$_N$CH$_2$OH {n=1(20%), 2 (31%), 3 (27%), 4 (16%), 5 (6%)} (yield 53 g, 83%). Each compound can be separated by fractional distillation under reduced pressure.

Example 13

Preparation of 3-Chloro-2,2,3-trifluoro-1-(4-vinyloxy-butoxy) propane H[ClFC—CF$_2$]$_1$CH$_2$—O—CH$_2$CH$_2$CH$_2$CH$_2$O—CH=CH$_2$ Step 1

Hydroxybutylvinylether (2.5 g, 21 mmol) was added dropwise to a stirred suspension of sodium tert-butoxide (2.30 g, 26.6 mmol) in 22 mL dry THF under nitrogen in such a way that the temperature of the reaction mixture did not exceed ~45° C. The resultant reaction mixture was cooled to ~45° C. and benzenesulfonyl chloride (3.5 g, 20 mmol) was added dropwise with stirring and gradually brought to room temperature.

Step 2

H[ClFC—CF$_2$]$_1$—CH$_2$OH (3.16 g, 21 mmol) was added dropwise to a stirred mixture of sodium tert-butoxide (2.30 g, 24 mmol) in 20 mL THF under nitrogen. After ~30 minutes stirring, the reaction mixture obtained in Step 1 was added to this solution and heated at ~75° C. for 4 hours. After this, the reaction mixture was concentrated under reduced pressure (40 mmHg) at 60° C., and to the mixture was added water (300 mL) and diethylether (200 mL) and mixed well. The ether layer was separated and concentrated and the resultant residue was distilled under reduced pressure to afford 1.6 g (yield 31%) of compound as a colorless liquid. B.P.=65–69° C./0.25 mmHg; GC/MS (EI mode): m/z at 246.6 for M$^+$; $^9$F and $^1$H NMR spectral data are consistent with the structure.

Example 14

Example 12 is repeated using ethyleneglycol vinylether and 1,4-cyclohexanedimethyl vinylether instead of hydroxybutyl vinyl ether to afford 3-chloro-2,2,3-trifluoro-1-(2-vinyl-ethoxy)propane H[ClFC—CF$_2$]$_1$CH$_2$—O—CH$_2$CH$_2$—O—CH=CH$_2$ and 3-chloro-2,2,3-trifluoro-1-[(4-vinyloxycyclohexyl)methoxy]-propane, respectively.

Example 15

Example 12 is repeated using various H[ClFC—CF$_2$]$_1$—CH$_2$OH (n=2, 3, 4, etc.) in Step 2 instead of H[ClFC—CF$_2$]$_1$—CH$_2$OH to obtain the compounds of formula H[ClFC—CF$_2$]$_n$—CH$_2$—O—X—O—CH=CH$_2$ (X=(CH$_2$)$_2$, (CH$_2$)$_4$, CH$_2$-cyclohexyl-CH$_2$—. . . etc.).

What is claimed is:

1. A polymer comprising one or more vinyl ether units having the formula:

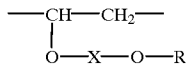

wherein R is a radical selected from the group consisting of R$_1$—C$_n$—H$_m$—, R$_1$—C$_n$H$_m$—C(=O)—, R$_1$—C$_n$H$_m$—CH[—O—X—O—CH=CH$_2$]C(=O—, R$_1$—C$_n$H$_m$—CH[—C(=O)—O—X—O—CH=CH$_2$], R$_1$—C$_n$H$_m$—CH[C(=O)—O—X—O—CH=CH$_2$—]C(=O)—, R$_1$—[CFCl—CF$_2$—]p CH$_2$— and HCFCl—CF$_2$—; wherein R$_1$ is selected from the group consisting of unsubstituted and substituted fluorinated aliphatic radicals, unsubstituted and substituted fluorinated cyclic aliphatic radicals, unsubstituted and substituted fluorinated aromatic radicals, unsubstituted and substituted fluorinated araliphatic radicals and unsubstituted and substituted fluorinated heterocyclic radicals; n is an integer between 1 and 6, inclusive; n≤m≤2n; p is an integer between 1 and 20, inclusive; and X is selected from the group consisting of unsubstituted and substituted aliphatic radicals, unsubstituted and substituted cyclic aliphatic radicals, un-substituted and substituted aromatic radicals, unsubstituted and substituted araliphatic radicals and unsubstituted and substituted heterocyclic radicals; provided that when R$_1$ of R$_1$—C$_n$H$_m$— is an otherwise unsubstituted fluorinated aliphatic radical, X is not ethylene or propylene.

2. The polymer of claim 1, wherein R contains at least 1 chlorine or bromine.

3. The polymer of claim 1, wherein R contains at least one radical selected from the group consisting of —OH, —COOCH$_3$, —OCH$_3$, —OCH$_2$CH$_3$, —NO$_2$SH, —SCH$_3$, phenyl, benzyl, cyclohexyl, cyclohexyldimethyl and chlorocylcohexyl radicals.

4. The polymer of claim 1, wherein R is selected from the group consisting of R$_1$—C$_n$H$_m$—, R$_1$—C$_n$H$_m$C(=O)—, R$_1$—[CFCl—CF$_2$]pCH$_2$—, H—[CFCl—CF$_2$]pCH$_2$— and HCFCl—CF$_2$—.

5. The polymer of claim 1, wherein R is R$_1$—CnH$_m$—CH[—O—X—O—CH=CH$_2$]—.

6. The polymer of claim 1, wherein R is: R$_1$—C$_n$H$_m$—CH[—O—X—O—CH=CH$_2$]—C(=O)— or R$_1$—C$_n$H$_m$—CH[—C(=O)—O—X—O—CH=CH$_2$]—.

7. The polymer of claim 1, wherein R is: R$_1$—C$_n$H$_m$—CH[—C(=O)—O—X—O—CH=CH$_2$]—C(=O)—.

8. The polymer of claim 4, 5, 6 or 7, wherein R$_1$ is a Cl—Cl$_2$ fluorinated aliphatic radical; and X is an aliphatic, cyclic aliphatic, aromatic or araliphatic radical.

9. The polymer of claim 8, wherein X is a 1,4-cyclohexyldimethyl radical or an alkyl radical having the formula (—CH$_2$—)$_n$, wherein n is between 2 and 4, inclusive.

10. The polymer of claim 9, wherein R$_1$ is a trifluoromethyl radical.

11. The polymer of claim 1, wherein said polymer further comprises one or more second repeating units selected from the group consisting of monomers, oligomers and polymers containing at least one terminal ethylenically unsaturated group and monomers, oligomers and polymers containing at least one terminal epoxide group.

12. The polymer of claim 1, consisting essentially of said vinyl ether repeating units.

* * * * *

UNITED STATES PATENT AND TRADEMARK OFFICE
CERTIFICATE OF CORRECTION

PATENT NO. : 6,743,943 B2
DATED : June 1, 2004
INVENTOR(S) : Russell F. Anderson et al.

It is certified that error appears in the above-identified patent and that said Letters Patent is hereby corrected as shown below:

Title page,
Item [75], Inventors, should read: -- Russell F. Anderson, David E. Bradley, David Nalewajek, Haridasan K. Nair, Mariola J. Proszowski, Eugene V. Sitzmann, and Ellen L. Swan --

Signed and Sealed this

Twenty-first Day of December, 2004

JON W. DUDAS
*Director of the United States Patent and Trademark Office*